US007033995B2

(12) United States Patent
Weiss et al.

(10) Patent No.: US 7,033,995 B2
(45) Date of Patent: Apr. 25, 2006

(54) PRODUCTION OF RADIAL GLIAL CELLS

(75) Inventors: Samuel Weiss, Calgary (CA); Christopher Gregg, Calgary (CA)

(73) Assignee: Stem Cell Therapeutics Inc., Calgary ( * ) Notice: Subject to any disclaimer, the term of this patent is extended or adjusted under 35 U.S.C. 154(b) by 185 days.

(21) Appl. No.: 10/196,549

(22) Filed: Jul. 17, 2002

(65) Prior Publication Data
US 2003/0032181 A1 Feb. 13, 2003

Related U.S. Application Data

(60) Provisional application No. 60/307,096, filed on Jul. 20, 2001.

(30) Foreign Application Priority Data
Nov. 30, 2001 (CA) ..................... 2364095

(51) Int. Cl.
*A61K 38/18* (2006.01)
(52) U.S. Cl. ........................... 514/2; 514/12; 435/377; 424/198.1
(58) Field of Classification Search ................ 435/7.2; 514/2; 530/399
See application file for complete search history.

(56) References Cited

U.S. PATENT DOCUMENTS

| 5,750,376 A | 5/1998 | Weiss et al. |
| 5,753,506 A | 5/1998 | Johe |
| 5,851,832 A | 12/1998 | Weiss et al. |
| 5,980,885 A | 11/1999 | Weiss et al. |

FOREIGN PATENT DOCUMENTS

WO 99/32606 A2 7/1999

OTHER PUBLICATIONS

Rajan et al. J. Neurosci. 1998, vol. 18, pp. 3620-3639.*
Kastin et al. Brain Res., 1999, vol. 848 (1-2), pp. 96-100.*
Kojima et al., J. Neuropathol. Exp. Neurol., 2000, vol. 59, pp. 687-697.*
Lindvall et al. Nature Medicine, 2004, suppl. to vol. 10, pp. s42-s50.*
Caviness VS. (1982) Neocortical histogensis in normal and reeler mice: a developmental study based upon [3H] thymidine autoradiography. Dev Brain Res. 4: 293-302.
Caviness VS Jr, Takahashi T, and Nowakowski RS. (1995) Numbers, time and neocortical neurogenesis: a general developmental and evolutionary model. TINS. 18(9): 379-383.
Edwards MA, Yamamoto M, and Caviness VS Jr. (1990) Organization of radial glia and related cells in the developing murine CNS. An analysis based upon a new monoclonal antibody marker. Neuroscience. 36(1):121-144.
Feng L, Hatten ME, and Heintz N. (1994) Brain lipid-binding protein (BLBP): A novel signaling system in the developing mammalian CNS. Neuron. 12: 895-908.
Frederiksen K and McKay RD. (1988) Proliferation and differentiation of rat neuroepithelial precursor cells *in vivo*. J Neurosci. 8: 1144-1151.
Gadisseux JF, Evrard PH, Mission JP, and Caviness VS Jr. (1992) Dynamic changes in the density of radial glial fibers of the developing murine cerebral wall: a quantitative immunohistological analysis. J Comp Neurol. 322: 246-254.
Hartfuss E, Galli R, Heins N, and Gotz M. (2001) Characterization of CNS precursor subtypes and radial glia. Developmental Biology. 229: 15-30.
Hatten ME and Heintz N. (1999) Neurogenesis and Migration. Fundamental Neuroscience. Ed. Zigmond MJ, Bloom FE, Landis SC, Roberts JL, Squire LR. Academic Press. San Diego, CA. 451-480.
Huttner WB and Brand M. (1997) Asymmetric division and polariity of neuroepithelial cells. Curr Opin Neurobiol. 7: 29-39.
Johansson CB, Momma S, Clarke DL, Risling M, Lendahl U, Frisen J. (1999) Identification of a neural stem cell in the adult mammalian central nervous system. Cell. 96(1):25-34.
Levitt P and Rakic P. (1980) Immunoperoxidase localization of glial fibrillary acidic protein in radial glial cells and astrocytes of the developing rhesus monkey brain. J Comp Neurol. 193: 815-840.
Malatesta P , Hartfuss E, and Gotz M. (2000) Isolation of radial glial cells by flourescent-activated cell sorting reveals a neuronal lineage. Development. 127: 5253-5263.
Mission JP, Edwards MA, Yamamoto M, and Caviness VS Jr. (1988a) Identification of radial glial cells within the developing murine central nervous system: studies based upon a new immunohistochemical marker. Dev Brain Res. 44:95-108.
Mission JP, Takahashi T, and Caviness VS Jr. (1991) Ontogeny of radial and other astroglial cells in murine cerebral cortex. Glia. 4: 138-48.
Noctor S, Flint AC, Weissman TA, Dammerman RS, and Kriegstein AR. (2001) Neurons derived from radial glial cells establish radial units in neocortex. Nature. 409: 714-720.

(Continued)

*Primary Examiner*—David S. Romeo
*Assistant Examiner*—Daniel C. Gamett
(74) *Attorney, Agent, or Firm*—Fish & Richardson P.C.

(57) ABSTRACT

The present invention relates to a method of producing radial glial cells from neural stem cells, particularly by contacting neural stem cells with epidermal growth factor (EGF), fibroblast growth factor 2 (FGF-2) and/or TGFα. Leukemia inhibitory factor (LIF) and ciliary neurotrophic factor (CNTF) can optionally be added to enhance the effect of EGF, FGF-1 or TGFα. Also provided are methods of producing radial glial cells from ependymal cells, as well as methods of proliferating ependymal cells.

7 Claims, 3 Drawing Sheets

OTHER PUBLICATIONS

Pixely SK and de Vellis J. (1984) Transition between immature radial glia and mature astrocytes studied with a monoclonal antibody to Vimentin. Dev Brain Res. 15: 201-209.

Shibata T, Yamada K, Watanabe M, Ikenaka K, Wada K, Tanaka K, Inoue Y. (1997) Glutamate transporter GLAST is expressed in the radial glia-astrocyte lineage of developing mouse spinal cord. J Neurosci. 17(23):9212-9219.

Shingo, T. et al. (2001) Erythropoietin Regulates the *In Vitro* and *In Vivo* Production of Neuronal Progenitors by Mammalian Forebrain Neural Stem Cells. J. Neuroscience. 21 (24):9733-9743.

Takahashi T., et al. (1990) Glial process elongation and branching in the developing murine neocortex: a qualitative and quantitative immunohistochemical analysis. J. Comp. Neurol. 302(1):15-28.

Tropepe V, Shibilia M, Ciruna BG, Rossant J, Wagner EF, and van der Kooy D. (1999) Distinct neural stem cells proliferate in response to EGF and FGF in the developing mouse telencephalon. Developmental Biology. 208: 166-188.

Voigt T. (1989) Development of glial cells in the cerebral wall of ferrets: direct tracing of their transformation from radial glia into astrocytes. J Comp Neurol. 289: 74-88.

Database Biosis "Online" Biosciences Information Services, Philadelphia, PA; 2001, Gregg, C.T., et al., "Generation of radial glial by embryonic neural stem cells", Database accession No. PREV 200100486843, *Society for Neuroscience Abstracts*, 27(1):344, 31st Annual Meeting of the Society for Neuroscience, San Diego, California (2001).

* cited by examiner

PRODUCTION OF RADIAL GLIAL CELLS

RELATED APPLICATIONS

This application claims the benefit of U.S. Provisional Applications Ser. No. 60/307,096, filed Jul. 20, 2001, and Canadian Patent Application No. 2,364,095, filed Nov. 30, 2001. The entire disclosure of each of these priority applications is hereby incorporated by reference.

FIELD OF THE INVENTION

This invention relates to a method for generating radial glial cells. In particular, neural stem cells proliferated in FGF-2 plus heparin sulfate, EGF or TGFα generate antigenically-identified radial glial cells.

References

U.S. Pat. No. 5,750,376.
U.S. Pat. No. 5,851,832.
U.S. Pat. No. 5,980,885.
Caviness V S. (1982) Neocortical histogensis in normal and reeler mice: a developmental study based upon [3H] thymidine autoradiography. Dev Brain Res. 4: 293–302.

Caviness V S Jr, Takahashi T, and Nowakowski R S. (1995) Numbers, time and neocortical neurogenesis: a general developmental and evolutionary model. TINS. 18(9): 379–383.

Edwards M A, Yamamoto M, and Caviness V S Jr. (1990) Organization of radial glia and related cells in the developing murine CNS. An analysis based upon a new monoclonal antibody marker. Neuroscience. 36(1): 121–144.

Feng L, Hatten M E, and Heintz N. (1994) Brain lipid-binding protein (BLBP): A novel signaling system in the developing mammalian CNS. Neuron. 12: 895–908.

Frederiksen K and McKay R D. (1988) Proliferation and differentiation of rat neuroepithelial precursor cells in vivo. J Neurosci. 8: 1144–1151.

Gadisseux J F, Evrard P H, Mission J P, and Caviness V S Jr. (1992) Dynamic changes in the density of radial glial fibers of the developing murine cerebral wall: a quantitative immunohistological analysis. J Comp Neurol. 322: 246–254.

Hartfuss E, Galli R, Heins N, and Gotz M. (2001) Characterization of CNS precursor subtypes and radial glia. Developmental Biology. 229: 15–30.

Hatten M E and Heintz N. (1999) Neurogenesis and Migration. Fundamental Neuroscience. Ed. Zigmond M J, Bloom F E, Landis S C, Roberts J L, Squire L R. Academic Press. San Diego, Calif. 451–480.

Huttner W B and Brand M. (1997) Asymmetric division and polarity of neuroepithelial cells. Curr Opin Neurobiol. 7: 29–39.

Johansson C B, Momma S, Clarke D L, Risling M, Lendahl U, Frisen J. (1999) Identification of a neural stem cell in the adult mammalian central nervous system. Cell. 96(1):25–34.

Levitt P and Rakic P. (1980) Immunoperoxidase localization of glial fibrillary acidic protein in radial glial cells and astrocytes of the developing rhesus monkey brain. J Comp Neurol. 193: 815–840.

Malatesta P, Hartfuss E, and Gotz M. (2000) Isolation of radial glial cells by flourescent-activated cell sorting reveals a neuronal lineage. Development. 127: 5253–5263.

Mission J P, Edwards M A, Yamamoto M, and Caviness V S Jr. (1988a) Identification of radial glial cells within the developing murine central nervous system: studies based upon a new immunohistochemical marker. Dev Brain Res. 44:95–108.

Mission J P, Takahashi T, and Caviness V S Jr. (1991) Ontogeny of radial and other astroglial cells in murine cerebral cortex. Glia. 4: 138–48.

Noctor S, Flint A C, Weissman T A, Dammerman R S, and Kriegstein A R. (2001) Neurons derived from radial glial cells establish radial units in neocortex. Nature. 409: 714–720.

Pixely S K and de Vellis J. (1984) Transition between immature radial glia and mature astrocytes studied with a monoclonal antibody to vimentin. Dev Brain Res. 15: 201–209.

Shibata T, Yamada K, Watanabe M, Ikenaka K, Wada K, Tanaka K, Inoue Y. (1997) Glutamate transporter GLAST is expressed in the radial glia-astrocyte lineage of developing mouse spinal cord. J Neurosci. 17(23):9212–9219.

Shingo, T. et al. (2001) Erythropoietin Regulates the In Vitro and In Vivo Production of Neuronal Progenitors by Mammalian Forebrain Neural Stem Cells. J. Neuroscience. 21(24):9733–9743.

Tropepe V, Sibilia M, Ciruna B G, Rossant J, Wagner E F, and van der Kooy D. (1999) Distinct neural stem cells proliferate in response to EGF and FGF in the developing mouse telencephalon. Developmental Biology. 208: 166–188.

Voigt T. (1989) Development of glial cells in the cerebral wall of ferrets: direct tracing of their transformation from radial glia into astrocytes. J Comp Neurol. 289: 74–88.

All of the publications, patents and patent applications cited in this application are herein incorporated by reference in their entirety to the same extent as if the disclosure of each individual publication, patent application or patent was specifically and individually indicated to be incorporated by reference in its entirety.

BACKGROUND OF THE INVENTION

Radial glial cells (RGCs) are one of the earliest cell types to appear in the developing central nervous system (CNS). RGCs function as neuronal progenitors, as well as a glial scaffold to support neuronal migration into the developing layers of the cerebral cortex. RGCs do not persist into the adult mammalian CNS. Instead, these cells transform into mature astrocytes and ependymal cells in the postnatal period of development.

It was believed that the adult mammalian brain was not capable of regenerating neurons. However, the recent discovery of adult neural stem cells (NSCs) demonstrates that multipotent neural stem cells are present in adult mammalian brains, which can proliferate and differentiate upon appropriate stimuli into all lineages of neural cells, including neurons and glial cells (astrocytes and oligodendrocytes). It therefore appears possible to generate neural cells using neural stem cells in the treatment of diseases or conditions caused by neural cell loss or damage. Nevertheless, proper maturation and migration of neuronal precursors would require radial glial cells, which are lacking in the adult mammalian brain. Consequently, it is desirable to reestablish a radial glial cell population in the adult mammalian brain, which will help to recapitulate developmental processes normally absent in the mature CNS, thereby aiding in the regeneration of damaged or diseased CNS tissue. Given that very little is known about the signals involved in the generation, differentiation, and postnatal transformation of RGCs, the need exists for a method of producing radial glial cells.

SUMMARY OF THE INVENTION

The present invention relates to a method of producing radial glial cells from neural stem cells, particularly by contacting neural stem cells with epidermal growth factor (EGF), fibroblast growth factor 2 (FGF-2) and/or TGFα. Leukemia inhibitory factor (LIF) and ciliary neurotrophic factor (CNTF) can optionally be added to enhance the effect of EGF, FGF-2 or TGFα.

Importantly, both embryonic and adult neural stem cells can be used to generate radial glial cells, thus the present invention is useful in the treatment of diseases or conditions caused by neural cell loss or damage in an adult animal. This method can be practiced in vivo by administering a radial glia promoting agent, such as EGF, FGF-2 or TGFα, into the brain of the diseased animal. Alternatively, neural stem cells can be cultured according to methods known in the art (see, e.g., U.S. Pat. Nos. 5,750,376; 5,980,885; 5,851,832), incubated according to the present invention to produce radial glial cells, and the resulting cells are then transplanted into an animal suffering from neural cell loss or damage.

Furthermore, we also found that ependymal cells can be induced to produce radial glial cells as well. In addition, ependymal cells can be proliferated efficiently with the combination of FGF-2 and heparin sulfate.

Accordingly, one aspect of the present invention provides a method for generating radial glial cells from neural stem cells, comprising contacting at least one neural stem cell with an effective amount of epidermal growth factor (EGF), fibroblast growth factor-2 (FGF-2) or transforming growth factor alpha (TGFα). Optionally, the neural stem cells can be contacted with ciliary neurotrophic factor (CNTF) or leukemia inhibitory factor (LIF) as well. In particular, the combination of EGF with CNTF and/or LIF can be used first, followed by TGFα.

The method can be practiced in vitro or in vivo. The neural stem cell is located preferably in a brain, more preferably in a mammalian brain, yet more preferably in a human brain, and most preferably in an adult human brain. Alternatively, the neural stem cell may be located in a cell culture, particularly one derived from a brain tissue. The brain tissue is preferably harvested from an adult mammal and most preferably harvested from an adult human.

Another aspect of the present invention provides a method of producing radial glial cells from ependymal cells, comprising contacting the ependymal cells with an effective amount of EGF, CNTF, LIF and/or TGFα. Preferably, the ependymal cells are contacted with the combination of EGF and CNTF. To increase the number of ependymal cells and ultimately production of radial glial cells from the enlarged ependymal cell population, FGF-2 can be used to induce proliferation of ependymal cells. Preferably, heparin sulfate is employed along with FGF-2, particularly when used in vivo to proliferate ependymal cells in situ.

Another aspect of the present invention provides a method for treating or ameliorating a central nervous system (CNS) disease or damage in a mammal, comprising transplanting radial glial cells into the mammal. The radial glial cell can be obtained by incubating neural stem cells in the presence of an effective amount of EGF, FGF-2 or TGFα, with the optional addition of CNTF or LIF. The CNS disease may be a neurodegenerative disease, particularly Alzheimer's Disease, Multiple Sclerosis (MS), Huntington's Disease, Amyotrophic Lateral Sclerosis, and Parkinson's Disease.

Another aspect of the present invention provides a method for enhancing neural cell mobilization in a mammal, comprising one selected from the group consisting of:
(a) administering to the mammal an effective amount of a radial glia promoting agent;
(b) transplanting radial glial cells into the mammal; and
(c) transplanting neural stem cell progeny into the mammal and inducing the transplant to form radial glial cells in the mammal.

The radial glia promoting agent is preferably EGF, FGF-2 or TGFα, with the optional addition of CNTF or LIF. The neural cell is preferably a neuron or neuron precursor. In (c), the transplant can be induced to form radial glial cells by, for example, administration of a radial glia promoting agent, which may be administered in any manner that results in production of radial glial cells. Preferably, the agent is administered into a ventricle of the brain, particularly the lateral ventricle.

Further provided by the present invention are compositions comprising radial glial cells. The radial glial cells may be produced by the methods described herein. The composition may further comprise a pharmaceutical acceptable excipient and/or a pharmaceutical acceptable carrier. Preferably, the composition is suitable for transplantation.

DETAILED DESCRIPTION OF THE INVENTION

Figure 1:
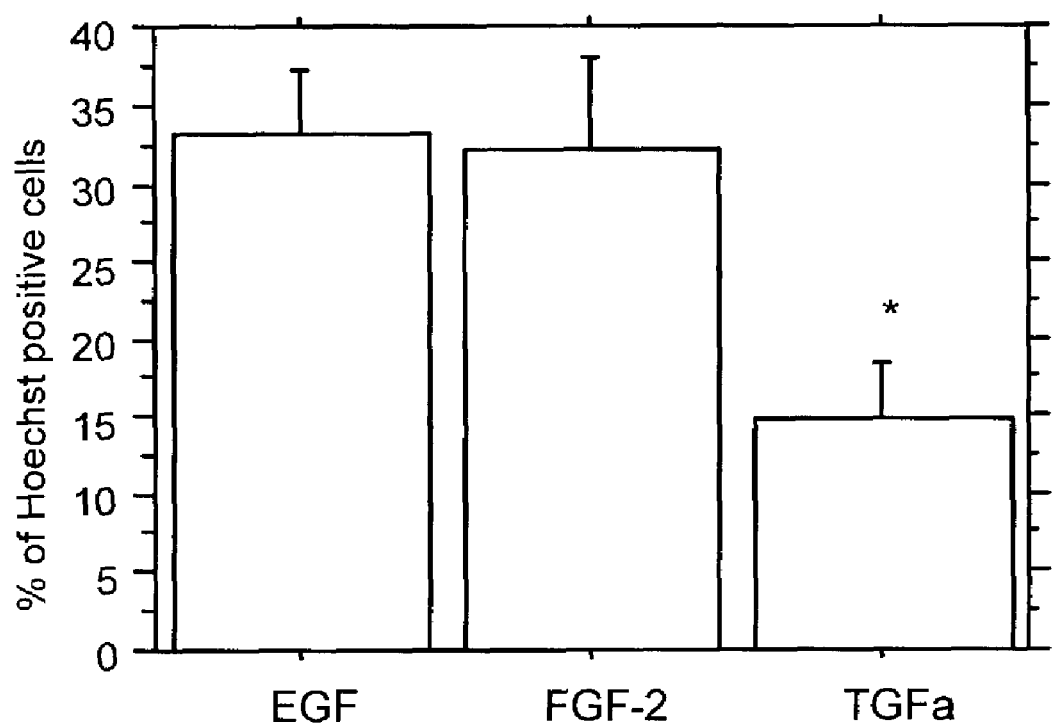
FIG. 1 Generation of cells expressing radial glial markers by neural stem cells can be differentially regulated by proliferation in the presence of FGF-2, EGF, or TGFα. Dissociated pass 1 neurospheres grown in either FGF-2+HS, EGF, or TGFα were plated on poly-L-ornithine coated coverslips for 30 minutes and immunolabeled with Hoechst, Nestin, and RC2. Cells double labeled for Nestin and RC2 were counted and expressed as a percentage of total Hoechst positive cells. (*$p<0.05$)

The present invention relates to a method of producing radial glial cells from neural stem cells or ependymal cells, particularly by contacting neural stem cells with epidermal growth factor (EGF), fibroblast growth factor 2 (FGF-2) and/or TGFα. Leukemia inhibitory factor (LIF) and ciliary neurotrophic factor (CNTF) can optionally be added to enhance the effect of EGF, FGF-2 or TGFα.

Importantly, both embryonic and adult neural stem cells can be used to generate radial glial cells, thus the present invention is useful in the treatment of diseases or conditions caused by neural cell loss or damage in an adult animal. This method can be practiced in vivo by administering a radial glia promoting agent, such as EGF, FGF-2 or TGFα, into the brain of the diseased animal. Alternatively, neural stem cells can be cultured according to methods known in the art (see, e.g., U.S. Pat. Nos. 5,750,376; 5,980,885; 5,851,832), incubated according to the present invention to produce radial glial cells, and the resulting cells are then transplanted into an animal suffering from neural cell loss or damage. Neural stem cells can also be transplanted and induced to form radial glial cells in vivo.

Prior to describing the invention in further detail, the terms used in this application are defined as follows unless otherwise indicated.

Definitions

A "radial glial cell" is a cell possessing either of the following properties: (1) antigenically, a radial glial cell expresses the intermediate filament nestin, and the intermediate-filament associated protein RC2; (2) morphologically, a radial glial cell is a bipolar cell extending long, thin processes from the soma ("radial morphology"). A radial glial cell is preferably a cell that stains positive with antibodies against RC2 and nestin, and more preferably a cell with the radial morphology. Most preferably, a radial glial cell has both the antigenic and morphological properties described above.

A "neural stem cell" is a stem cell in the neural cell lineage. A stem cell is a cell which is capable of reproducing itself. Therefore, when a stem cell replicates, at least some of the daughter cells (progenitor cells) are also stem cells. The neural stem cells, and their progenitor cells, are capable of differentiating into all the cell types in the neural cell lineage, including neurons, astrocytes and oligodendrocytes (astrocytes and oligodendrocytes are collectively called glia or glial cells). In other words, the neural stem cells are multipotent neural stem cells.

"Neural stem cell progeny" refers to any cell or collection of cells that is derived from a neural stem cell. The progeny may comprise, for example, daughter neural stem cells, neuronal precursor cells, glial precursor cells, neurons and glial cells.

"Pass 1 neural stem cells" are neural stem cells which have been passaged once in culture. Typically, neural stem cells can be obtained from an embryo or an adult brain tissue (for example the subventricular zone of the forebrain) and plated as a primary culture (see, for example, U.S. Pat. No. 5,750,376). The primary culture can then be dissociated and re-plated. The resulting cells, which have been passaged once in culture, are called the pass 1 neural stem cells.

A "neurosphere" is a group of cells derived from a single neural stem cell as the result of clonal expansion.

A "neural cell", as used herein, refers to a neuron, glia, or a precursor thereof.

A "neuron precursor" or "neuronal precursor" is a cell that is destined to become a neuron. In particular, a neuron precursor expresses known markers for neuron progenitor, for example, MASH1.

The term "neural cell migration" means the change of location of a neural cell. In particular, this term refers to the migration associated with the process whereby neuronal precursors mature into neurons.

A "neurodegenerative disease or condition" is a disease or medical condition associated with neuron loss or dysfunction. Examples of neurodegenerative diseases or conditions include neurodegenerative diseases, brain injuries or CNS dysfunctions. Neurodegenerative diseases include, for example, Alzheimer's Disease, Multiple Sclerosis (MS), Huntington's Disease, Amyotrophic Lateral Sclerosis, and Parkinson's Disease. CNS dysfunctions include, for example, depression, epilepsy, neurosis and psychosis.

"Treating or ameliorating" means the reduction or complete removal of the symptoms of a disease or medical condition.

An "effective amount" is an amount of a therapeutic agent sufficient to achieve the intended purpose. For example, an effective amount of EGF to produce radial glial cells from neural stem cells is an amount sufficient to induce detectable radial glial cell formation, in vivo or in vitro. An effective amount of a radial glia promoting agent to treat or ameliorate a neurodegenerative disease or condition is an amount of the agent sufficient to reduce or remove the symptoms of the neurodegenerative disease or condition. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

A "radial glia promoting agent" is a chemical compound or mixture of chemical compounds that is capable of inducing radial glial cell formation from neural stem cells in vitro or in vivo according to the methods disclosed in the present invention. The radial glia promoting agent is preferably EGF, FGF-2, TGFα, CNTF and/or LIF, more preferably EGF or TGFα, and most preferably EGF.

"Transplanting" a composition into a mammal means introducing the composition into the body of the mammal using any methods known in the art. The composition being transplanted is a "transplant", and the mammal is the "recipient".

1. Radial Glial Cells

Radial glial cells are typically identified antigenically in the mouse as cells which express the intermediate filament protein nestin (Frederiksen and McKay, 1988), the intermediate-filament associated protein RC2 (Mission et al., 1988), brain lipid binding protein (BLBP) (Feng et al., 1994), and later in development glial fibrillary acidic protein (GFAP) (Mission et al., 1991). Morphologically these cells are bipolar with one short thin process extending apically with an endfoot at the ventricular surface, and a second long thin process extending basally across the entire cortical wall, terminating with an endfoot at the glial limitans membrane of the cortical surface.

The classification of radial glial cells is somewhat enigmatic. These cells have been classified as glial cells, likely for two major reasons. First, their identification in the primate cortex (Levitt and Rakic, 1980) revealed that they express the astrocyte maker GFAP, although they do not express this protein until late in development in rodents (Mission et al., 1991). The second reason is that these cells are known to transform into glial cell types postnatally, in particular astrocytes (Voigt, 1989; Takahashi et al., 1990). For these reasons radial glial cells are considered part of the glial cell lineage.

Besides being recognized as glial cells, radial glia have also been purported to be a type of neuroepithelial cell (Huttner and Brand, 1997). Radial glial cells express the neuroepithelial cell marker nestin as previously noted, their soma resides in the ventricular zone, and they undergo interkinetic movements during cell division similar to classic neuroepithelial cells (Noctor et al., 2001; Mission et al., 1988). Further, the radial glial cell population has been demonstrated to be composed of progenitor cells, capable of producing both neurons and glia (Noctor et al., 2001; Malatesta et al., 2000). Thus, it is difficult to accurately classify them simply as glial cells. Therefore, while radial glial cells are clearly a part of the astroglial lineage, these cells may also be considered a subtype of neuroepithelial cell.

During the earliest stages of neural development, following neural induction, the neural plate consists of a single cell layer of pseudostratified ventricular neuroepithelium (PVE) (Hatten and Heintz, 1999). Neuroepithelial cells actively proliferate, first dividing symmetrically, expanding their population and then asymmetrically, giving rise to additional cell types (reviewed in Huttner and Brand, 1997). In the mouse, early E11 marks the onset of cortical neurogenesis in the cerebral PVE, as this is the first time at which postmitotic neurons can be observed (reviewed in Caviness et al., 1995). RC2 positive cells first appear among the cells of the PVE at E9 in caudally developing structures, but appear between E10–E11 in more rostral areas (Mission et al., 1988a). Thus, the appearance of these cells correlates with the onset of neurogenesis.

Radial glial cells actively divide throughout neurogenesis (Hartfuss et al., 2001; Malatesta et al., 2000), giving rise to neurons which migrate out of the ventricular zone to the marginal zone of the developing cortex along the radial glial processes which extend from the radial glial soma across the cortical wall to the glial limitans (Noctor et al., 2001). This process of migration requires the expression of a neural glycoprotein called astroctactin (Hatten and Heintz, 1999).

From approximately E11–E14, the density of radial glial fibers increases in the developing cortex, and the number of fibers which extend across the entire cortical wall reaches a maximum density at E14 (Gadisseux et al., 1992). During this stage the large pyramidal neurons destined to occupy layer V in the adult have occupied their postmigratory positions in radially aligned columns (Caviness, 1982). Also, at this stage approximately 50% of radial fibers extend across the entire cerebral wall to the pial surface, while the remaining fibers extend to a zone just below the subplate and with a growth cone at the terminal end of their process (Gadisseux et al., 1992). Note that during this period all radial glial cells appear to be bipolar, with their soma residing in the ventricular zone.

At E15, a secondary germinal zone, the subventricular zone (SVZ), is evident immediately superficial to the ventricular zone (VZ). At this time point bipolar radial glial cells translocate their soma from the VZ into the SVZ (Gadisseux et al., 1992). From E15 to E17, a massive surge of neurons is generated, giving rise to cells which will occupy the supragranular cortical layers II and III. Concurrent with this stage of neuron birth is the surge of the radial fibers at the subplate up into the cortical plate out to the marginal zone (Gadisseux et al., 1992). These fibers are likely to support the migration of the newly generated granular neurons, as well as arrange them into ascending bundles which intercalate the more massive ontogenic columns formed during the first stage of neuron birth (Gadisseux et al., 1992).

E17 marks the cessation of neurogenesis and the beginning of gliogenesis. This is the first appearance of a monopolar form of radial glial cell which lacks its descending process (Mission et al., 1991). The soma of many of these cells has translocated into the intermediate zone and more superficial layers of the cerebral wall by this time. As well, the basal process begins to branch both from the shaft and the tip of the radial fiber. This arborization process continues postnatally, and the dominating bipolar phenotype is gradually replaced with a monopolar form. Finally, the monopolar form of radial glia undergoes a final transition into a multipolar astrocyte, which persists into adulthood throughout the cortical layers (Voigt, 1989; Takahashi et al., 1990; Pixely and de Vellis, 1984; Mission et al., 1991). It is also suspected that radial glial cells are likely to give rise to other glial cells postnatally including ependymal cells, a ciliated cell which lines the ventricles (Edwards et al., 1990).

Very little is known about the signals which regulate the development of radial glial cells. The signals which give rise to these cells during development are not known, nor is it understood which signals are involved in the transition of these cells into astrocytes and ependymal cells, or why NSCs do not generate these cells in adulthood.

2. FGFR1 and EGFR Signaling in the Regulation of RGC Development

FGF-2 expression can be detected as early as E9.5 in the telencephalon. The FGF-2 protein levels increase dramatically during early neurogenesis and then decline from mid to late neurogenesis. The FGF-2 receptor, FGFR-1 is expressed as early as E8.5–E9.5 in the murine telencephalon and is largely confined to the ventricular zone during later stages of development. Both EGF and TGFα are expressed in the telencephalon at very early stages of CNS development, as is the EGFR. In order to better establish a role for FGFR-1 and EGFR signaling in the regulation of RGC development we analyzed the expression of these receptors by RGCs in the germinal zone of the ganglionic eminence at the beginning of neurogenesis (approximately E11.5 in the mouse) and during midneurogenesis (E14.5).

We found that both FGFR-1 and EGFR were expressed in the neuroepithelium at the onset of neurogenesis. Furthermore, RGCs, defined by RC2 expression, were found to express both FGFR-1 and EGFR at E11 and E14. These findings indicate a role for FGFR-1 and EGFR signaling in the regulation of the RGC lineage beginning at very early stages of CNS development.

3. Methods for Producing Radial Glial Cells

We investigated the ability of embryonic or adult neural stem cells (NSCs) to give rise to cells which antigenically and morphologically resemble radial glia. It was found that three known NSC mitogens, FGF-2, EGF and TGFα, differentially regulated the generation of radial glia by NSCs, as determined by the number of RC2+nestin double-labeled cells produced within neurospheres (Example 1). The order of efficacy was EGF>FGF-2>>TGFα. CNTF and/or LIF can further enhance the production of radial glial cells (Example 2)

Despite exhibiting antigenic markers of radial glia, these neurosphere-derived cells were unable to adopt a radial morphology when differentiated in basal media alone. However, radial morphology can be induced by EGF or TGFα (Example 3). Optionally, CNTF or LIF can be included to further enhance the development of radial morphology. FGF-2, however, does not support radial morphology formation of these cells.

Radial glial cells of the present invention are capable of supporting neural cell migration. For example, neurospheres produced in the presence of EGF extended long thin processes that contained radial glial cell markers GLAST (Shibata et al., 1997), nestin, BLBP and vimentin. These processes extended outward and eventually reach other neurospheres. Cells that resemble neuron precursors could be observed to move along these processes from one neurospheres to another. These moving cells stained positive for the early nueronal markers beta-III-tubulin, Hu, and double-courtin (Example 4). Therefore, the radial glia promoting agents of the present invention induced the formation of radial glial cells that antigenically, morphologically and functionally resemble radial glial cells of the developing brain.

These factors can also be used in vivo to produce radial glial cells. We tested whether adult cells were capable of adopting a radial glial phenotype in response to these same signals by infusing EGF, TGFα, or FGF-2 plus heparin sulfate (HS) into the lateral ventricles of adult mice (Example 6). All three factors resulted in the generation of RC2 expressing cells around the entire circumference of the lateral ventricles. Furthermore, the RC2 positive cells in EGF or TGFα infused mice had a clearly elongated, radial morphology, while the RC2 expressing cells in FGF-2 infused mice expressed GFAP and had a multipolar astrocytic morphology. Therefore, these factors can induce radial glial cell formation in vivo, Importantly, even though radial glial cells normally disappear in the postnatal stage in mammals, we demonstrate that adult mammals can be induced to produce radial glial cells by the present method.

In addition to neural stem cells, we discovered that ependymal cells can form radial glial cells as well (Example 7). Ependymal cells are the epithelial cells that form the lining of ventricles in the CNS. Upon infusion of EGF or TGFα, ependymal cells extended a long, thin process perpendicular to the surface of the ventricle towards the parenchyma. Although adopting a radial morphology, these cells did not express radial glial cell markers. When both EGF and CNTF were administered to the animals, however, ependymal cells lost their characteristic marker, s100beta, began to express radial glial cell markers, and adopted a radial morphology. Therefore, ependymal cells are capable of forming radial glial cells.

Although it has been proposed that ependymal cells are neural stem cells, our results do not support this hypothesis. Neural stem cells are known to proliferate in response to EGF. However, ependymal cells did not proliferate in EGF-infused mice. Proliferation of ependymal cells can be induced by administering FGF-2 and HS (Example 8), thereby increasing the number of ependymal cells and further facilitating production of radial glial cells from ependymal cells. It should be noted that it is particularly effective to administer HS along with FGF-2. While heparin sulfate is produced at high levels in the embryonic ventricular zone during neurogenesis, it appears to be at a very low level in the adult ventricles. It is therefore important to provide heparin sulfate along with FGF-2.

It is contemplated that radial glia promoting agents other than EGF, FGF-2 and TGFα can further be identified using the methods disclosed herein. Moreover, variants or analogs of EGF, FGF-2, TGFα, LIF and CNTF that have radial glia promoting activities are also contemplated in the present invention. A variant or analog useful in the present invention is a protein that is capable of binding to the receptor of the native factor, as well as possessing at least about 30% amino acid sequence identity with the native factor. For example, an EGF analog contemplated herein should be capable of competing with a native mammalian EGF (for example, the 53 amino acid native human EGF) for binding with the receptor of the native mammalian EGF. In addition, the analog should display at least about 30% sequence identity when compared to the amino acid sequence of the native mammalian EGF. The sequence identity is preferably at least about 40%, more preferably at least about 50%, yet more preferably at least about 60%, still more preferably at least about 70%, and most preferably at least about 80%. The efficacy of the analog in promoting radial glia formation can be determined according to the present invention.

The presence of neural stem cells (NSCs) and other cells capable of proliferation in the CNS suggests a great deal of potential for the repair of CNS tissue through either endogenous mobilization or transplantation strategies. However, while methods exist to either trigger the proliferation of NSCs in vivo, or to transplant these cells into the brain, the problems of how to promote the migration of NSC progeny to a site of injury, as well as how to organize these newly generated cells into the highly complex structure of the brain, represent a major challenge. During development, the processes of cell migration and organization are largely mediated by the radial glial cells. The present invention thus opens the door of treating or ameliorating CNS diseases or damages with the aid of radial glial cells produced according to the disclosure herein.

Mobility of neural cells, particularly neurons or neuron precursors, can be enhanced by administering at least one radial glia promoting agent to a mammal as disclosed herein. Alternatively, neural stem cell progeny can be cultured in vitro and transplanted into a mammal. The neural stem cell progeny may comprise radial glial cells produced as described above. In addition, at least radial glia promoting agent can be administered into the recipient mammal concurrently with or after performance of the transplantation.

While generally useful, such treatment will prove particularly valuable for the elderly. As adult mammals, the elderly have no radial glial scaffold in their brains, and they suffer a higher risk of neurodegenerative diseases. Neurodegenerative diseases include the diseases which have been linked to the degeneration of neural cells in particular locations of the central nervous system (CNS), leading to the inability of these cells to carry out their intended function. These diseases include Alzheimer's Disease, Multiple Sclerosis (MS), Huntington's Disease, Amyotrophic Lateral Sclerosis, and Parkinson's Disease.

In addition, probably the largest area of CNS diseases or conditions (with respect to the number of affected people) is not characterized by a loss of neural cells but rather by abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis. Moreover, brain injuries often result in the loss of neural cells, the inappropriate functioning of the affected brain region, and subsequent behavior abnormalities. Treatment or amelioration of these diseases and conditions, too, will benefit from the production of radial glial cells, which form a scaffold to support neuronal migration to the locations suitable for proper neuronal functions.

4. Compositions of the Present Invention

Another aspect of the present invention provides compositions that can be used to produce radial glial cells. The compositions of this invention comprise at least one radial glia promoting agent, particularly EGF, FGF-2 or TGFα. FGF-1 containing compositions preferably also comprise heparin sulfate, particularly for administration into the brain. The composition can optionally comprise an accessory factor, such as LIF or CNTF. The composition may further comprise a pharmaceutically acceptable excipient and/or carrier.

For in vivo administrations, the composition can be delivered via any route known in the art, such as intravascularly, intramucularly, transdermally, subcutaneously, or intraperitoneally. Preferably, the composition is delivered into the CNS. Most preferably it is delivered into a ventricle of the brain, particularly the lateral ventricle.

Also provides are compositions comprising radial glial cells, particularly the radial glial cells produced by the methods described herein. The radial glial cell composition may further comprise a pharmaceutically acceptable excipient and/or carrier. Preferably, the composition is suitable for transplantation.

The following examples are offered to illustrate this invention and are not to be construed in any way as limiting the scope of the present invention.

EXAMPLES

In the examples below, the following abbreviations have the following meanings. Abbreviations not defined have their generally accepted meanings.

| | |
|---|---|
| ° C. = | degree Celsius |
| hr = | hour |
| min = | minute |
| µM = | micromolar |
| mM = | millimolar |
| ml = | milliliter |
| µl = | microliter |
| mg = | milligram |
| µg = | microgram |
| ng = | nanogram |
| BLBP = | brain lipid binding protein |
| CNS = | central nervous system |
| CNTF = | ciliary neurotrophic factor |
| DIV = | days in vitro |
| DMEM = | Dulbecco's modified Eagle's medium |
| EGF = | epidermal growth factor |
| EGFR = | epidermal growth factor receptor |
| FBS = | fetal bovine serum |
| FGF = | fibroblast growth factor |
| FGFR = | fibroblast growth factor receptor |
| GFAP = | glial fibrillary acidic protein |
| HS = | heparin sulfate |
| LIF = | leukemia inhibitory factor |
| LIFR = | leukemia inhibitory factor receptor |
| NSC = | neural stem cell |
| PBS = | phosphate buffered saline |
| PVE = | pseudostratified ventricular neuroepithelium |
| RGC = | radial glial cell |
| SVZ = | subventricular zone |
| TGF = | transforming growth factor |
| VZ = | ventricular zone |

General Materials and Methods

Neural Stem Cell Culture

The composition of basal media, or MHM, is as follows: DMEM/F12 (1:1); glucose (0.6%); glutamine (2 mM); sodium bicarbonate (3 mM); HEPES (5 mM); insulin (25 µg/ml); transferrin (100 µg/ml); progesterone (20 nM); putrescine (60 µM); and selenium chloride (30 nM) (all from Sigma, except glutamine from Life Technologies).

Embryonic NSCs were cultured as neurospheres from tissue dissected from the ganglionic eminence of E14 CD-1 mouse using the methods previously described by Shingo et al. (2001). NSCs were grown in the presence of FGF-2 (20 ng/ml; R&D Systems) and heparin sulfate (2 µg/ml), EGF (20 ng/ml; Peprotech), or TGFα (20 ng/ml; Gibco or Peprotech). Adult neurosphere cultures were performed as described by Shingo et al. (2001) in the presence of EGF containing media (20 ng/ml) from 2–3 month old CD-1 male mice.

Cells were grown for 7 DIV and formed floating neurosphere clusters. These primary spheres were pelleted, dissociated and plated into culture flasks at 50,000 cells/ml in growth media. After 7 DIV, second generation (pass 1) neurospheres were differentiated in the radial glial cell outgrowth assay as described below, or were treated as follows. Neuropheres were rinsed in basal media, dissociated and plated at a density of 200,000 cells/ml onto poly-L-ornithine coated coverslips for 30 minutes in 300 ml of basal media, just to allow cells to settle. Cells were then fixed in 4% paraformaldehyde and processed for immunocytochemistry.

For immunocytochemistry, neurospheres were allowed to settle in 15 ml Falcon tubes for 15–20 min, after which the media was removed and replaced with 4% paraformaldehyde for 20 minutes at room temperature. The paraformaldehyde was then aspirated off and was replaced with 10% sucrose in PBS overnight at 4° C. followed by 25% sucrose in PBS overnight at 4° C. The sucrose was aspirated off, the neurospheres were embedded and frozen in a cryomold, cryosectioned at 14 mm, and processed for immunocytochemistry.

Clonal Density Cultures

To generate neurospheres clonally, pass 1 neurospheres were dissociated and cells were plated at a density of 72 cells/ml in a 2 ml volume of EGF containing growth media in 6 well plates (Nunc). After 5 DIV, an additional 1 ml of fresh EGF containing growth media was added. Cells were cultured for a total of 10–12 DIV to allow neurospheres to form. Clonally-derived neurospheres were then used in the radial glial cell outgrowth assay as described below.

Radial Glial Cell Outgrowth Assay

To assess the ability of different growth factors to control the elongation of radial glial cells pass 1 neurospheres, grown in either FGF-2+HS, EGF, or TGFα for 7 DIV, were allowed to settle for 15–20 minutes in a Falcon tube. The growth factor containing media was aspirated off and spheres were rinsed in basal media. Individual neurospheres, 150–200 mm in diameter, were transferred to a poly-L-ornithine coated 96 well plate (Nunc) containing either FGF-2+HS, EGF, or TGFα at a density of 30–40 spheres per well. The spheres were then cultured for a further 5 DIV to allow for the formation of RGC processes between the spheres and where then either quantified or processed for immunocytochemistry.

To assess the presence of migrating neurons, growth media was removed and replaced with basal media for 48 hours to allow for the differentiation of neurons upon the radial glial fibers. Processing for immunocytochemistry was performed by gently removing the growth media with a pipet and adding 4% paraformaldehyde in PBS for 30 minutes, wells were then gently washed with PBS by changing solutions using a pipet. All primary antibodies were applied overnight at 4° C. and secondary antibodies were applied for 2 hrs at room temperature. Photos were taken microscope through the bottom of the culture plates using an inverted flourescent.

Immunocytochemistry and Immunohistochemistry

Primary antibodies used to were mouse anti-RC2 (neat, Developmental Hybridoma Bank; 1:100), mouse anti-nestin (neat, Developmental Hybridoma Bank), rabbit anti-nestin (1:100); rabbit anti-GFAP (1:400; BTI; 1:800; Sigma), mouse anti-beta-III-tubulin (1:500, Sigma), mouse anti-Hu (1:20, Molecular Probes), rabbit anti-GLAST (1:100), mouse anti-Vimentin (1:100), and rabbit anti-BLBP (1:800).

For immunocytchemical analysis on embryonic tissue sections timed pregnant CD-1 mice were sacrificed on embryonic day 14 and the brain was removed from embryos, fixed in 4% paraformaldehyde for 2 hours on ice, and then cryoprotected with 25% sucrose overnight. For adult tissue sections, 6–8 week old mice were perfused with 4% paraformaldehyde, the brains were dissected and placed in 4% paraformaldehyde overnight at 4° C., and then cryoprotected overnight in 10%, followed by 25% sucrose. All tissue was embedded in O.C.T. compound and cryosectioned at 14 mm. Tissue was analyzed using antibodies previously listed, as well as, mouse anti-s100beta (1:1000, Sigma) and sheep anti-EGFR (1:50, BTI). Primary antibodies were followed by incubation with flourescein or rhodamine-conjugated secondary antibodies against mouse, sheep, or rabbit IgG or by using biotin-conjugated secondary antibodies followed by CY3-streptavidin (Jackson Labs).

Intracerebral Ventricular Infusions

Intracerebral ventricular infusions were performed as described by Shimazaki et al. (2000) using 2–3 month old CD-1 male mice. Either FGF-2 (33 mg/ml)+HS (33 mg/ml), EGF (33 mg/ml), or TGFα (33 mg/ml) was infused intracerebroventricularly for 6 days at a rate of 0.5 ml/hr using an osmotic pump (Alzet 1007D; Alza Corporation, Palo Alto, Calif.) after which time animals were sacrificed for analysis.

Example 1

Generation of Radial Glial Cells From Neural Stem Cells

In order to assess the ability of EGF, TGFα, and FGF-2+HS to modulate the generation of radial glial cells from NSCs, neurospheres were generated from the E14 ganglionic eminence, a time point at which radial glial fibers reach their maximum density in the cortical wall, and NSCs which respond to each of the mitogens are present. Primary neurospheres were generated in the presence of 20 ng/ml of EGF, TGFα, or FGF-2. Two µg/mL of HS was added to FGF-2 cultures. After 7 days in culture, neurospheres were passaged into identical growth conditions to enhance clonality. Following a further 7 days in culture, spheres were dissociated with a brief trypsin-EDTA treatment and mechanical dissociation with a fire-polished pipet. Dissociated cells were plated onto poly-L-ornithine coated coverslips at a density of 200,000 cells/coverslip, and allowed to settle for 30 minutes, after which time they were fixed in 4% paraformaldehyde. Cells were then immunolabeled for RC2, nestin, and Hoechst. Blind counts for cells expressing both RC2 and Nestin were performed and expressed as a percentage of total Hoechst positive cells.

As shown in FIG. 1, the generation of cells which express radial glial markers can be differentially regulated by NSC growth in the presence of FGF-2+HS, EGF, or TGFα. Growth in EGF or FGF-2+HS promoted the generation of the greatest number of RC2+nestin double-labeled cells. Therefore, radial glial cells can be produced from neural stem cells.

Example 2

The Effect of LIF and CNTF

Primary neurospheres grown in the presence of FGF-2+HS, EGF, or TGFα for 7 days were passaged into identical growth conditions in the absence or presence of either LIF or CNTF. After 7 days passaged neurospheres were dissociated using trypsin and mechanical dissociation with a fire-polished pipet. Cells were plated onto poly-L-ornithine coated coverslips for 30 minutes, fixed in 4% paraformaldehyde, and immunolabeled for RC2, nestin, and Hoechst. Cells that were double labeled for RC2+nestin were counted (blind) in each condition and expressed as a percentage of total Hoechst positive cells.

Figure 2:
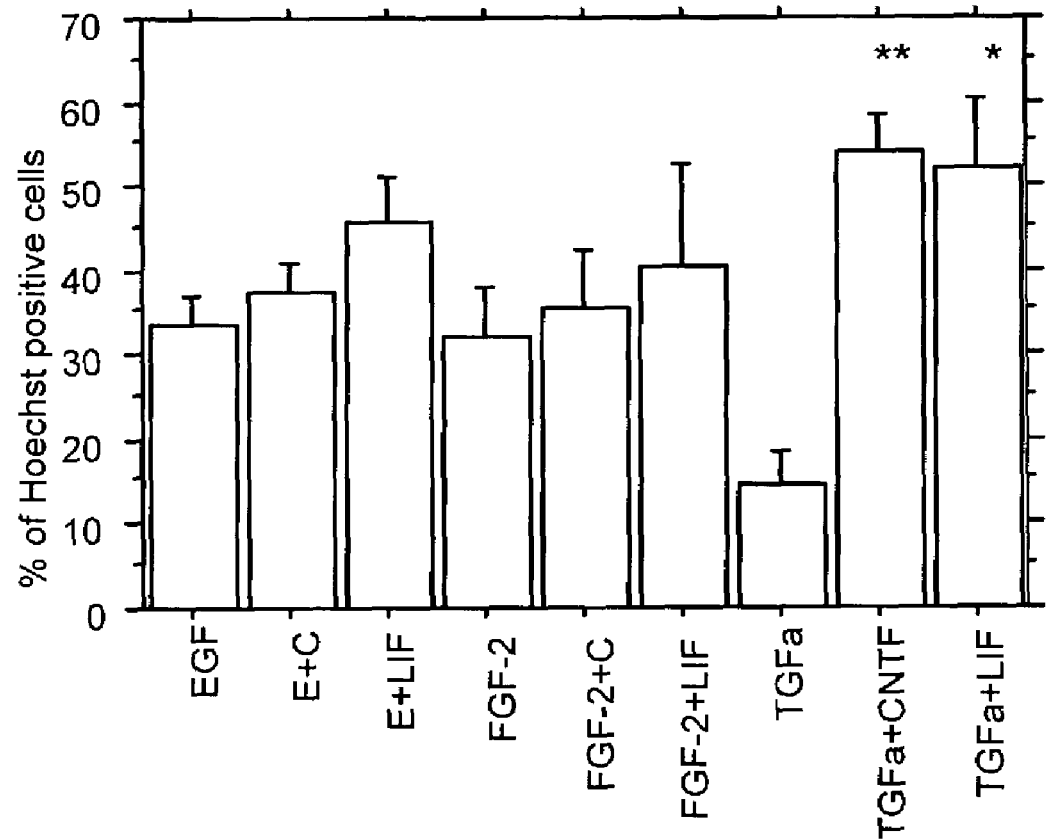
FIG. 2 Neural stem cell growth in the presence of LIF or CNTF modestly enhances the percentage of RC2+Nestin expressing cells produced in the FGF-2 and EGF growth conditions, but greatly enhances the percentage of these cells in the TGFα growth condition. (**$p<0.005$; *$p<0.05$; n=4)

The results (FIG. 2) indicate that NSC proliferation in the presence of either LIF or CNTF slightly increases the percentage of RC2+nestin co-expressing cells generated in EGF or FGF-2+HS proliferation conditions. In contrast, these cytokines significantly increased the percentage of presumptive radial glial cells in the TGFα growth condition. The increase in the number of radial glial cells, however, was the greatest when CNTF was combined with FGF, because the neurospheres doubled in size under these conditions and the total number of cells was high.

Example 3

Radial Morphology Formation Requires the Presence of Growth Factors

Previous experience indicates that a differentiation time of 5 DIV was sufficient for neural stem cell progeny to differentiate into GFAP expressing astrocytes and beta-tubulin III expressing neurons in basal media, without additional factors. To determine if the RC2+nestin positive cells described in Example 1 and 2 can differentiate to cells with a radial morphology, 7 DIV pass 1 E14 neurospheres grown in EGF were rinsed in basal media and plated down on poly-L-ornithine coated 96 well plates in the presence of basal media as described in Materials and Methods. After 5 DIV, the morphology of differentiated cells was examined. We could find no evidence of any cells which morphologically resembled radial glia in these conditions (n=3). Further, analysis of cells from dissociated neurospheres also did not reveal cells having a radial morphology when plated in basal media. These findings suggested that signals required for the induction of radial morphology were absent from the basal media differentiation condition.

To investigate which factors can promote radial morphology formation, we grew E14 pass 1 neurospheres in the presence of either FGF-2, EGF, or TGFα for 7 DIV. Individual neurospheres, 150–200 mm in diameter, were transferred to 96 well plates as previously described, at a density of 30–40 spheres per well, in the presence of various factors. After 5 DIV the percentage of spheres extending at least one radial glial process was determined.

Figure 3:
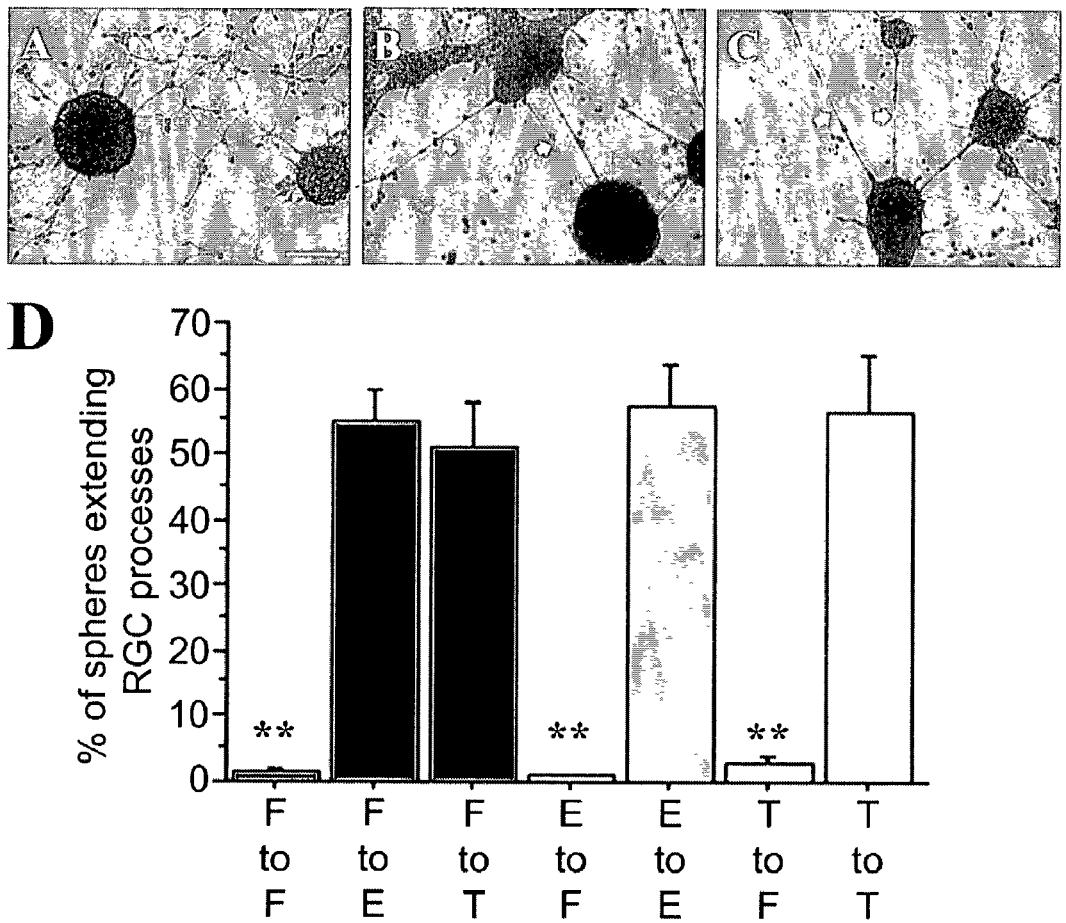
FIG. 3 EGF (panel B) and TGFα (panel C) support differentiation of RC2+Nestin expressing cells but not FGF-2 (panel A). Differentiation of RC2+Nestin expressing cells is indicated by the cells adopting the radial morphology, particularly the extension of long, thin processes (arrowheads). The results are quantified in panel D, wherein "F to F" indicates that the cells were grown in the presence of FGF-2 to neurospheres and then placed in differentiation conditions with FGF-2. Similarly, "E" stands for EGF and "T" stands for TGFα. (**$p<0.005$)

As shown in FIG. 3, over 50% of neurospheres generated in FGF-2 gave rise to radial glial processes when differentiated in the presence of either EGF (54.9±5.1%) or TGFα (51.0±7.0%; n=3). Similarly, 57.5±6.0% of EGF spheres gave rise to RGC processes when differentiated in EGF and 56.3±8.7% of TGFα neurospheres gave rise to RGC processes when differentiated in TGFα. In contrast, almost none of the spheres gave rise to RGC processes when differentiated in the presence of FGF-2 (n=3; p<0.01). This finding was independent of whether the spheres were generated in FGF-2, EGF or TGFα. These results thus demonstrate that EGF and TGFα were found to be equally capable of supporting RGC differentiation. However, while FGF-2 is capable of promoting the generation of RGCs that stain positive for RC2 and nestin, it is not capable of promoting the differentiation of these cells.

Example 4

Neuronal Migration Upon Radial Glia Formation

To observe the function of radial glial cells produced according to the present invention, pass 1 neurospheres grown in EGF were plated upon poly-L-ornithine coated 96 well plates in, the presence of EGF for 5 DIV. The neurospheres extended long thin processes out from the spheres, which generally extended along the floor of the dish to contact other neurospheres. After contacting another sphere, the processes no longer rested upon the floor of the plate, but floated in the media, extending like a tight rope between the spheres. Small cells appeared to be migrating upon these long processes and the morphology of the processes and the migrating cells were strikingly similar to previous in vitro descriptions of neurons migrating upon radial glia.

We reasoned that there are two possible cell types which have an elongated morphology and support neuronal migration: neurons extending long neurites and radial glia. In order to distinguish between these two cell types we immunolabeled the cells for markers that are specific for neuronal processes and radial glial processes, respectively. We found that the long radial-glia like processes did not express the neurite marker beta-III-tubulin, but expressed the RGC markers GLAST, nestin, BLBP, and vimentin, indicating that these processes belong to radial glial cells.

In order to determine whether the radial glial cells generated in response to EGF were actively supporting neuronal migration, we employed time lapse microscopy in order to observe the cells on the RGC processes over time to determine whether in fact they were migrating. E14 pass 1 neurospheres were grown at a clonal density of 72 cells/ml in the presence of EGF. After 10 DIV individual clonally-derived neurospheres were plated in 96 well plates at a density of 30–40 neurospheres per well in the presence of EGF and were analyzed after 5 DIV. Clonally-derived neurospheres gave rise to RGC processes similar to those observed in the batch cultures described above (n=3). Presumptive neurons, photographed every 10 minutes over a 195 minute period, actively migrated along glial processes from one sphere toward a second sphere and ultimately could be seen entering the opposing sphere. The migrating cells morphologically resembled migrating immature neurons, having a leading process and displaying a pattern of saltatory migration.

We immunolabeled these cells to determine if they are neurons. When the cells were fixed immediately after 5 DIV in EGF, none of the cells expressed the early neuronal markers beta-III-tubulin or Hu. Since these markers are normally not upregulated until immature neurons exit the germinal zone, we hypothesized that withdrawal of growth factors might be necessary in order to induce differentiation and expression of these markers. To test this hypothesis, we washed out the EGF-containing media after 5 DIV and replaced it with basal media for a further 2 DIV to induce spontaneous differentiation of the presumptive neurons. Indeed, at this point, the cells migrating along the RGC process could be clearly identified with the neuronal markers beta-III-tubulin, Hu, and doublecourtin. These results thus demonstrate that the radial glia-like cells generated by NSCs in response to EGF functionally resemble radial glia by actively supporting neuronal migration. Therefore, NSCs give rise to cells which morphologically, antigenically and functionally resemble radial glial cells of the developing brain in response to EGF.

Example 5

Adult Neural Stem Cells are Capable of Forming Radial Glial Cells

Radial glial cells do not exist in adult mammals. Adult neural stem cells, however, have been shown to proliferate and differentiate into neurons and glial cells in the same manner as embryonic neural stem cells. Therefore, we tested the ability of adult neural stem cells to produce neural stem cells.

Neurospheres were generated from adult brain tissue as described in Materials and Methods, and pass 1 neurospheres were labeled for BLBP and nestin. The results show that adult neural stem cells also had the capacity to generate radial glia-like cells even though these cells are absent from the adult CNS (n=4).

Example 6

Radial Glial Cell Production In Vivo

We have demonstrated that both embryonic and adult NSCs are able to give rise to RGCs in vitro in response to EGF. These data therefore indicate that adult NSCs retain the capacity to form RGCs despite the fact that RGCs are no longer present in the adult brain. In order to determine whether adult NSCs are able to give rise to radial glia in vivo we infused either FGF-2+HS, EGF, or TGFα into the lateral ventricles of adult mice for 6.5 days. Mice were then sacrificed and analyzed by immunohistochemistry for the presence of RGCs. In all three conditions RC2 expressing cells were generated around the entire circumference of the lateral ventricles while no RC2 expression was observed around the lateral ventricles of the mice that received the vehicle control, indicating that adult neural stem cells can be induced by growth factors to form radial glial cells in the brain in situ.

In order to further analyze the RC2 expressing cell population in the infused animals we used z-stacked confocal images to study morphology of the cells. The RC2 expressing cell population in the FGF-2+HS infused animals had a multipolar astrocytic morphology and did not display the elongated morphology indicative of RGCs. This finding is consistent with our previous data demonstrating that FGF-2 does not support the radial morphology of RGCs. In contrast, an analysis of EGF and TGFα infused animals revealed that the RC2 expressing cell population had a clearly elongated, radial morphology. The soma was located at the ventricular surface while single, basal radial processes extended into the surrounding parenchyma.

The radial RC2 expressing cell population in the EGF and TGFα infused animals also expressed the RGC markers BLBP and nestin. Moreover, the majority of RC2 expressing cells in the FGF-2+HS infused animals robustly expressed GFAP, whereas RC2 expressing cells in the EGF infused animals did not express GFAP and those in the TGFα infused animals expressed very low levels of GFAP. These findings therefore demonstrate that adult NSCs are capable of giving rise to RGCs in the adult forebrain in response to either EGF or TGFα. Under these experimental conditions, FGF-2 generated cells expressed RC2, had an astrocytic morphology and expressed the astroglial marker GFAP.

Therefore, EGF, FGF-2 and TGFα can be used to produce radial glial cells in vivo. In particular, EGF or TGFα can induce the formation of radial glial cells that are positive for radial glial cell markers and radial morphology.

Example 7

Ependymal Cells Adopt a Radial Glial Morphology in Response to EGF or TGFα

It has been suggested that ependymal cells may be a remnant of the embryonic VZ and more recently that this cell population may represent a population of NSCs in the adult forebrain and spinal cord (Johansson et al., 1999). We investigated whether the infusion of signals which promote the RGC phenotype might induce ependymal cells to adopt a radial glial phenotype. Infusions of FGF-2 plus HS, EGF or TGFα were performed as previously described. Ependymal cells were identified using the ependymal cell specific marker s100beta.

In vehicle control infusions, the ependymal layer was a thin, single cell layer composed of cuboidal cells adjacent to the ventricular surface. In both EGF and TGFα infused animals, ependymal cells underwent a dramatic alteration in morphology. Thus, 48.9±14.9% (n=4) of ependymal cells in EGF infused animals and 66.9±5.9% (n=3) of ependymal cells in TGFα infused animals extended a long thin basal process perpendicular to the surface of the ventricle towards the parenchyma. In contrast, in FGF-2 infused mice, ependymal cells did not adopt a radial morphology, though a very small number (2.2±1.0%; n=3) did appear to extend a short basal process away from the ventricular surface in some cases. FGF-2 also appeared to dramatically upregulate s100beta expression in the SVZ.

Double labeling of s100beta with the RGC markers BLBP, RC2, and nestin revealed that the ependymal cells in EGF and TGFα infused animals did not express radial glial markers though they displayed a radial morphology. Interestingly, some regional differences were observed in the morphology displayed by the ependyma in the EGF infused, and particularly the TGFα infused, animals. Cells along the lateral and medial aspects of the ventricles extended single basal processes in a surprisingly organized manner, with all processes extending perpendicular to the ventricular surface. Occassionally, some ependymal cells along the medial side of the ventricle translocated their soma away from the ventricle leaving a short apical process with an endfoot contacting the ventricular surface, this phenomenon was never observed among ependymal cells on the lateral aspects of the ventricles. Rather, translocation of the soma of ependymal cells away from the ventricular surface was most commonly observed dorsally. Some of these cells clearly displayed a bipolar radial morphology, having a short apically located process and a longer basal process which was generally deflected by the corpus collosum, apparently unable to penetrate these dense white matter tracts. The ependymal cell processes were generally restricted to the zone of expansion around the lateral ventricles, with the endfoot of the process terminating at the border between the expansion zone and the brain parenchyma.

Although ependymal cells produced radial glial cells that do not express radial glial cell markers in response to EGF or TGFα, the combination of EGF and CNTF resulted in dramatic radial glial cell production from ependymal cells. Upon infusion of EGF and CNTF, ependymal cells no longer expressed s100beta. Instead, the cells expressed radial glial cell markers and adopted a radial morphology. Therefore, although EGF and TGFα can each induce radial glial cell formation, the combination of EGF and CNTF is much more effective.

Example 8

Ependymal Cells Proliferate in Response to FGF but not EGF

As shown above, ependymal cells, like neural stem cells, adopt a radial morphology in response to EGF infusion. Since it was previously proposed that ependymal cells may be neural stem cells, which proliferate in response to EGF, we determined whether ependymal cells also proliferated in response to EGF infusion. Six to eight week old mice received BrdU injections every 2 hours for 12 hours on the 6th day of EGF infusion and were analyzed by double-labeling for BrdU and s100beta. We analyzed the contralateral ventricles of 3 infused mice, 12 sections per mouse, by confocal microscopy. We were unable to find a single unambiguous BrdU positive ependymal cell. However, BrdU positive, s100beta negative cells could be observed intercalated with ependymal cells. The inability of ependymal cells to proliferate in response to EGF therefore indicates that they are not neural stem cells.

We discovered that ependymal cells proliferate in response to FGF and/or its cofactor heparin sulfate (HS). A six day infusion of FGF-2 and HS induced a massive proliferation of the ependymal cell layer. Interestingly, infusion of FGF-2 alone had only a weak effect. Since we found that ependymal cells, and cells of the subventricular zone, do not contain detectable levels of HS, our results indicate that heparin sulfate is a limiting factor that restricts ependymal cell proliferation in the adult mammalian brain. Consistent with this notion, heparin sulfate is produced at high levels in the embryonic ventricular zone during neurogenesis. We therefore infused heparin sulfate alone into the adult forebrain, and proliferation of ependymal cells as well as in the subventricular zone was increased.

Accordingly, ependymal cells can be induced to produce radial glial cells by using EGF and/or TGFα, and in particular the combination of EGF and CNTF/LIF. Furthermore, the number of ependymal cells can be increased by using FGF-2 or heparin sulfate, preferably both. CNTF nad/or LIF can be further used to increase the number of ependymal cells in the presence of FGF-2. It is contemplated that maximal radial glial cell formation can be achieve by inducing both ependymal cell increase and radial glial cell production from ependymal cells, for example by using FGF-2, HS, LIF, EGF and CNTF.

We claim:

1. A method for generating radial glial cells from neural stem cells located in the brain of a postnatal mammal, comprising contacting at least one neural stem cell in the brain with an effective amount of at least one radial glia promoting agent as well as ciliary neurotrophic factor (CNTF) and/or leukemia inhibitory factor (LIF), wherein the radial glia promoting agent is selected from the group consisting of epidermal growth factor (EGF), fibroblast growth factor-2 (FGF-2) and transforming growth factor alpha (TGFα).

2. The method of claim 1 wherein the mammal is an adult.

3. The method of claim 1 wherein the mammal is a human.

4. The method of claim 1 wherein the neural stem cell is contacted with EGF and LIF, followed by TGFα.

5. The method of claim 1 wherein the neural stem cell is contacted with EGF and CNTF, followed by TGFα.

6. A method of producing radial glial cells from ependymal cells in a postnatal mammal, comprising contacting the ependymal cells with an effective amount of EGF and at least one of CNTF and LIF.

7. The method of claim 6 wherein the ependymal cells are further contacted with TGFα.

* * * * *